US010624781B2

(12) United States Patent
Ivri

(10) Patent No.: US 10,624,781 B2
(45) Date of Patent: Apr. 21, 2020

(54) MICRO-DROPLET DELIVERY DEVICE AND METHODS

(71) Applicant: Kedalion Therapeutics, Inc., Menlo Park, CA (US)

(72) Inventor: Yehuda Ivri, Newport Beach, CA (US)

(73) Assignee: Kedalion Therapeutics, Inc., Menlo Park, CA (US)

( * ) Notice: Subject to any disclaimer, the term of this patent is extended or adjusted under 35 U.S.C. 154(b) by 593 days.

(21) Appl. No.: 14/992,975

(22) Filed: Jan. 11, 2016

(65) Prior Publication Data

US 2016/0199225 A1    Jul. 14, 2016

Related U.S. Application Data

(60) Provisional application No. 62/125,073, filed on Jan. 12, 2015.

(51) Int. Cl.
| | | |
|---|---|---|
| *A61F 9/00* | (2006.01) | |
| *A61F 9/04* | (2006.01) | |
| *H01L 41/09* | (2006.01) | |
| *A61M 11/00* | (2006.01) | |
| *F04B 43/04* | (2006.01) | |

(52) U.S. Cl.
CPC .......... *A61F 9/0008* (2013.01); *F04B 43/046* (2013.01)

(58) Field of Classification Search
CPC ........ A45D 2200/057; A45D 2200/207; A61F 9/0008; A61F 9/0026; A61H 35/02; A61M 11/005; A61M 15/0085; A61M 15/025; B01L 2400/0436; B01L 2400/0439; F04B 43/046; H01L 41/09; H01L 41/0986

See application file for complete search history.

(56) References Cited

U.S. PATENT DOCUMENTS

| | | |
|---|---|---|
| 3,812,854 A | 5/1974 | Michaels et al. |
| 3,976,072 A | 8/1976 | Walker |
| 4,159,803 A | 7/1979 | Cameto et al. |
| 4,300,546 A | 11/1981 | Kruber |
| 4,334,531 A | 6/1982 | Reichl et al. |
| 4,338,576 A | 7/1982 | Takahashi et al. |

(Continued)

FOREIGN PATENT DOCUMENTS

| | | |
|---|---|---|
| CN | 104146816 A | 11/2014 |
| EP | 622035 A1 | 11/1994 |

(Continued)

OTHER PUBLICATIONS

Oxford online dictionary entry for "stream." https://en.oxforddictionaries.com/definition/us/stream. Accessed Thu Dec. 13, 2018.*

(Continued)

*Primary Examiner* — Adam Marcetich
(74) *Attorney, Agent, or Firm* — Lumen Patent Firm

(57) ABSTRACT

Micro-droplet delivery devices and methods are described where the device may comprise a piezoelectric actuator having a piezoelectric chip that is operatively coupled to a drug package under a preloading force. The actuator is configured to generate an acoustic pressure within the drug package to dispense droplets of an agent from an aperture, e.g., to the corneal surface of the eye. The piezoelectric actuator can be coupled or decoupled from the drug package.

22 Claims, 8 Drawing Sheets

(56) References Cited

U.S. PATENT DOCUMENTS

| | | |
|---|---|---|
| 4,352,459 A | 10/1982 | Berger et al. |
| 4,465,234 A | 8/1984 | Maehara et al. |
| 4,632,311 A | 12/1986 | Nakane et al. |
| 4,655,393 A | 4/1987 | Berger |
| 4,850,534 A | 7/1989 | Takahashi et al. |
| 4,961,345 A | 10/1990 | Tsuruoka et al. |
| 4,981,625 A | 1/1991 | Rhim et al. |
| 5,171,306 A | 12/1992 | Vo |
| 5,232,363 A | 8/1993 | Meller |
| 5,368,582 A | 11/1994 | Bertera |
| 5,487,378 A | 1/1996 | Robertson et al. |
| 5,624,057 A | 4/1997 | Lifshey |
| 5,627,611 A * | 5/1997 | Scheiner ............... A61F 9/0008 351/158 |
| 5,630,793 A | 5/1997 | Rowe |
| 5,657,926 A | 8/1997 | Toda |
| 5,938,117 A | 8/1999 | Ivri |
| 5,958,342 A * | 9/1999 | Gamble ............... B01J 19/0046 347/1 |
| 6,062,212 A | 5/2000 | Davison et al. |
| 6,232,129 B1 * | 5/2001 | Wiktor .................... B01L 3/021 422/417 |
| 6,467,476 B1 | 10/2002 | Ivri et al. |
| 6,543,442 B2 * | 4/2003 | Gonda ............... A61M 15/0045 128/200.14 |
| 6,629,646 B1 | 10/2003 | Ivri |
| 6,758,837 B2 | 7/2004 | Peclat et al. |
| 7,066,398 B2 | 6/2006 | Borland et al. |
| 7,201,732 B2 | 4/2007 | Anderson et al. |
| 7,883,031 B2 | 2/2011 | Collins et al. |
| 8,012,136 B2 | 9/2011 | Collins et al. |
| 8,128,606 B2 | 3/2012 | Anderson et al. |
| 8,133,210 B2 | 3/2012 | Al-Abdulla et al. |
| 8,273,307 B2 | 9/2012 | Eickhoff et al. |
| 8,398,001 B2 | 3/2013 | Borland et al. |
| 8,435,544 B2 | 5/2013 | Mitra et al. |
| 8,545,463 B2 | 10/2013 | Collins et al. |
| 8,684,980 B2 | 4/2014 | Hunter et al. |
| 8,722,728 B2 | 5/2014 | Wong et al. |
| 8,733,935 B2 | 5/2014 | Ballou, Jr. et al. |
| 8,936,021 B2 | 1/2015 | Collins |
| 9,039,666 B2 | 5/2015 | Voss et al. |
| 9,068,566 B2 | 6/2015 | Ivri |
| 9,087,145 B2 | 7/2015 | Ballou et al. |
| 9,597,230 B2 | 3/2017 | Haffner et al. |
| 2001/0036424 A1 * | 11/2001 | Takahashi ............ B01J 19/0046 422/504 |
| 2001/0036449 A1 | 11/2001 | Garst |
| 2002/0078947 A1 * | 6/2002 | Gumaste .......... A61M 15/0045 128/200.14 |
| 2002/0124843 A1 * | 9/2002 | Skiba .................... A61M 11/02 128/200.18 |
| 2002/0158196 A1 * | 10/2002 | Berggren ............ H01J 49/0454 250/288 |
| 2003/0065294 A1 * | 4/2003 | Pickup ................. A01K 11/005 604/304 |
| 2004/0050861 A1 * | 3/2004 | Lisec ..................... B01L 3/022 222/57 |
| 2004/0163645 A1 * | 8/2004 | Connelly .......... A61M 15/0028 128/203.15 |
| 2004/0215157 A1 | 10/2004 | Peclat et al. |
| 2004/0256487 A1 | 12/2004 | Collins et al. |
| 2005/0006417 A1 * | 1/2005 | Nicol .................... B01L 3/0241 222/420 |
| 2005/0172962 A1 | 8/2005 | Gumaste et al. |
| 2005/0261641 A1 | 11/2005 | Warchol et al. |
| 2006/0069358 A1 * | 3/2006 | Gerondale ............ A61F 9/0008 604/298 |
| 2006/0147313 A1 * | 7/2006 | Zengerle ............... B01L 3/0268 417/53 |
| 2007/0119969 A1 | 5/2007 | Collins et al. |
| 2007/0195151 A1 * | 8/2007 | Anderson ............ B41J 2/16505 347/109 |
| 2007/0268340 A1 * | 11/2007 | Dacquay ............... A61F 9/0017 347/68 |
| 2008/0202514 A1 * | 8/2008 | Kriksunov ........... A61M 11/005 128/203.15 |
| 2008/0233053 A1 | 9/2008 | Gross et al. |
| 2008/0247264 A1 * | 10/2008 | Gabl .................... B01F 11/0266 366/127 |
| 2009/0060793 A1 * | 3/2009 | Eickhoff ................ G01N 35/10 422/400 |
| 2009/0114742 A1 | 5/2009 | Collins, Jr. et al. |
| 2009/0134235 A1 | 5/2009 | Ivri |
| 2009/0182291 A1 * | 7/2009 | Eilat ................... A61F 9/0026 604/290 |
| 2009/0192443 A1 | 7/2009 | Collins, Jr. et al. |
| 2009/0212127 A1 | 8/2009 | Reynolds et al. |
| 2009/0212133 A1 | 8/2009 | Collins, Jr. et al. |
| 2009/0223513 A1 * | 9/2009 | Papania ............. A61M 15/0065 128/200.16 |
| 2010/0013352 A1 | 1/2010 | Pletner et al. |
| 2010/0044460 A1 | 2/2010 | Sauzade |
| 2010/0222752 A1 | 9/2010 | Collins, Jr. et al. |
| 2010/0295420 A1 | 11/2010 | Wierach |
| 2011/0074247 A1 | 3/2011 | Hohlfeld et al. |
| 2011/0102735 A1 * | 5/2011 | Gupta .................... G02C 5/143 351/158 |
| 2011/0106025 A1 | 5/2011 | Hall et al. |
| 2012/0017898 A1 | 1/2012 | Moller |
| 2012/0070467 A1 | 3/2012 | Ballou et al. |
| 2012/0143152 A1 | 6/2012 | Hunter et al. |
| 2012/0179122 A1 * | 7/2012 | Eilat ................... A61F 9/0026 604/290 |
| 2012/0304929 A1 * | 12/2012 | Ivri ....................... F04B 43/046 118/712 |
| 2013/0017283 A1 | 1/2013 | Zemel et al. |
| 2013/0345672 A1 | 2/2013 | Tanikawa et al. |
| 2013/0118619 A1 | 5/2013 | Loth et al. |
| 2013/0150812 A1 * | 6/2013 | Hunter .................. A61F 9/0008 604/295 |
| 2013/0152796 A1 | 6/2013 | Pawl |
| 2013/0153677 A1 * | 6/2013 | Leen ..................... B01L 3/0268 239/102.1 |
| 2013/0172830 A1 | 7/2013 | Hunter et al. |
| 2013/0206857 A1 | 8/2013 | Ivri |
| 2013/0299607 A1 | 11/2013 | Wilkerson et al. |
| 2013/0053042 A1 | 12/2013 | Ferreri et al. |
| 2014/0171490 A1 | 6/2014 | Gross et al. |
| 2014/0187969 A1 | 7/2014 | Hunter et al. |
| 2014/0224267 A1 | 8/2014 | Levitz et al. |
| 2014/0242022 A1 | 8/2014 | Vehige et al. |
| 2014/0249491 A1 | 9/2014 | Ballou, Jr. et al. |
| 2014/0257172 A1 | 9/2014 | Yalamanchili |
| 2014/0274910 A1 | 9/2014 | Cumberlidge et al. |
| 2014/0276054 A1 | 9/2014 | Hossack et al. |
| 2014/0285121 A1 | 9/2014 | Balogh et al. |
| 2014/0336618 A1 | 11/2014 | Wilkerson et al. |
| 2015/0018781 A1 | 1/2015 | Rinderknect et al. |
| 2015/0097050 A1 | 4/2015 | Ciervo |
| 2015/0144128 A1 * | 5/2015 | Hijlkema ............ B05B 17/0638 128/200.16 |
| 2015/0209174 A1 * | 7/2015 | Abreu ..................... A61F 7/02 607/104 |
| 2016/0199225 A1 | 7/2016 | Ivri |
| 2016/0296367 A1 | 10/2016 | Ivri |
| 2017/0156927 A1 * | 6/2017 | Richter ................ A61M 11/065 |
| 2017/0187969 A1 | 6/2017 | Kitamori et al. |
| 2017/0344714 A1 | 11/2017 | Ballou, Jr. et al. |

FOREIGN PATENT DOCUMENTS

| | | |
|---|---|---|
| JP | 3055480 U | 1/1999 |
| WO | WO 2001/046134 | 6/2001 |
| WO | WO 2013/090459 | 6/2013 |
| WO | WO 2013/090468 | 6/2013 |
| WO | WO 2013/155201 | 10/2013 |
| WO | WO 2013/158967 | 10/2013 |

(56) References Cited

FOREIGN PATENT DOCUMENTS

WO     WO2016115050 A1     7/2016
WO     WO2016164830 A1     10/2016

OTHER PUBLICATIONS

Merriam-Webster online dictionary entry for "stream." https://www.merriam-webster.com/dictionary/stream. Accessed Thu Dec. 13, 2018.*

Vocabulary.com online dictionary entry for "stream." https://www.vocabulary.com/dictionary/stream. Accessed Thu Dec. 13, 2018.*

Murube, J. et al., "Classification of artificial tears: I. Composition and properties," *Adv Exp Med Biol.*, 438:693-704: 49, 1998a.

Murube, J. et al., "Classification of artificial tears: II. Additives and commercial formulas," *Adv Exp Med Biol.*, 438:705-715, 1998b.

Jow, U. et al., "Design and Optimization of Printed Spiral Coils for Efficient Transcutaneous Inductive Power Transmission" *IEEE Transactions On Biomedical Circuits and Systems*, vol. 1, No. 3, pp. 193-202, Sep. 2007.

Communication—The extended European search report dated Jul. 23, 2018, European patent application No. 16737682.1, 8 pages.

Choi et al., Generation of controllable monodispersed sprays using impulse jet and charging techniques, Review of Scientific Instruments 61, 1689 (1990).

Lindblad et al., Production of uniform-sized liquid droplets, Journal of Scientific Instruments, vol. 42, No. 8, 1965.

Lux et al., A Comparative Bioavailability Study of Three Conventional Eye Drops Versus a Single Lyophilisate, British Journal of Ophthalmology, Apr. 2003, vol. 87, No. 4, pp. 436-440.

* cited by examiner

Detail-A  FIG-6

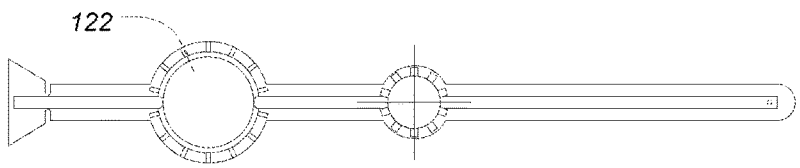
FIG-9B
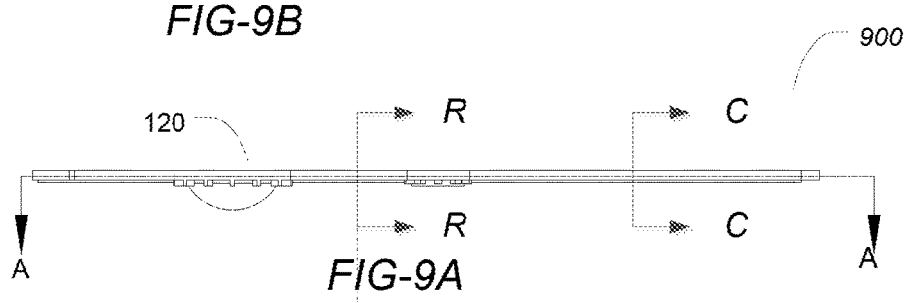
FIG-9A
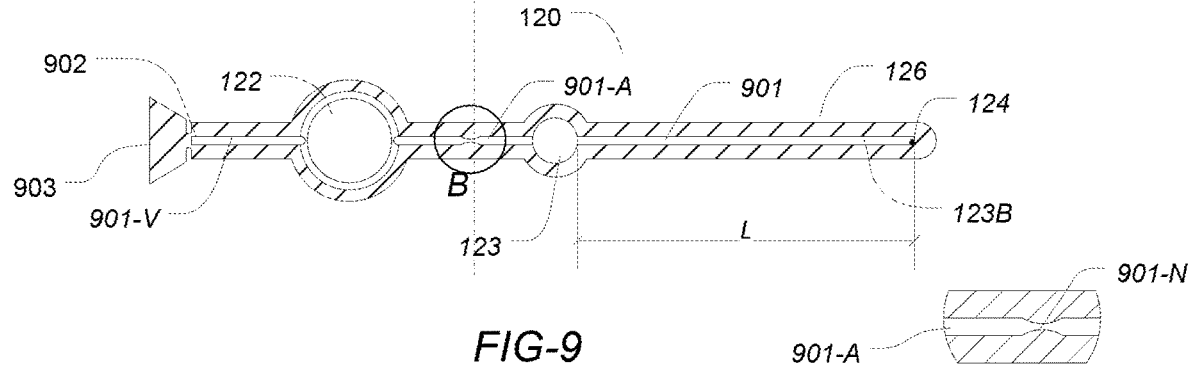
FIG-9
Detail B
FIG-9C

MICRO-DROPLET DELIVERY DEVICE AND METHODS

CROSS-REFERENCE TO RELATED APPLICATIONS

This application claims the benefit of priority to U.S. Prov. App. 62/125,073 filed Jan. 12, 2015, which is incorporated herein by reference in its entirety.

FIELD OF THE INVENTION

This disclosure relates to devices and methods for delivering one or more agents into onto a tissue region such as the surface of the eye to treat any number of conditions, e.g., moderate to severe cases of chronic dry eye syndrome (DES) by means of continuous delivery of replacement tears.

BACKGROUND OF THE INVENTION

DES is caused by deficiency of tear production with symptoms of ocular dryness, grittiness, pain, continuous discomfort, visual disturbance, burning and stinging sensation and a risk of corneal damage.

Current treatments is primarily palliative includes supplemental eye drops which act as artificial tears to provide temporary relief and to protect the ocular surface. However, severe cases of DES require very frequent administration, which is often impractical to follow. Thus, in severe DES the irritative symptoms described above persists and can be debilitating in both psychological and physical effects. DES has an impact on quality of life due to degradation of vision-related daily activities, bodily pain and continuous discomfort.

The present invention overcomes the impractically of frequent administration. The invention provides a disposable ampoule discreetly attachable to an eyewear article and configured to continuously or intermittently project ultra-small droplets towards the surface of the eye at a rate that provides adequate tear replacement.

BRIEF SUMMARY OF THE INVENTION

The invention provides a miniature wearable micro-droplet ejection device for treatment chronic dry eye syndrome. The device comprises a disposable drug package and a piezoelectric actuator. The drug package is configured to dispense micro-droplets by means of acoustic pulse exerted by the piezoelectric actuator onto the external surface of the disposable drug package. In the present invention the drug package can be decoupled from the piezoelectric actuator allowing disposal of used packages while the piezoelectric actuator is reused with another drug package. The invention provides an economical and cost effective approach for the treatment of any number of conditions for which delivery of one or more agents is desirable. Treatments for the condition of chronic DES is described herein for illustrative purposes only as the devices and methods described may be applied to any number of different conditions and for the delivery of any number of agents not limited to the treatment of DES.

The piezoelectric actuator is removably attached to an earpiece of an eyewear article such as optical or sunglasses, by means of pressure sensitive adhesive, a mechanical spring-clip or the like. The disposable drug package is inserted into the actuator such that the dispensing nozzle is extended toward the lens of eyewear article and then bent backwardly over the surface of the lens toward the of the eye. Droplets are dispensed toward the surface of the eye based on predetermined time interval at a rate and accumulative volume that provides adequate tear replacement. The dispensing rate can be adjusted based on the patient tear production deficiency which may be determined by basal secretion test such as, but not limited to Schirmer's test procedure.

In one embodiment the drug package is comprised of a blow-fill-seal package or an ampoule containing preservative-free ophthalmic formulation of tears replacement. The formulation may comprise of an aqueous solution containing polymers such as polyvinyl alcohol, povidone hydroxypropyl, methyl cellulose, poloxamers, carboxymethyl or cellulose hydroxyethyl.

Various formulations for treatment of dry eye syndrome which may be used in the device of the present invention were disclosed in PCT patent publication WO 2001/046134 A1 and in U.S. Pat. Pubs. 2013/053042 A1, 2014/0274910 A1, 2014/0242022 A1, 2001/0036449 A1, 2012/0070467 A1 and in U.S. Pat. No. 8,722,728 B2.

The composition may include anti-inflammatory topical corticosteroids such as tetracyclines, Cyclosporine pilocarpine, or cyclosporine A.

Application of autologous serum or umbilical cord serum may also be used in moderate to severe cases of DES.

Artificial tears formulations which are disclosed in the following publications may also be used:
1. Murube J, Paterson A, Murube E. Classification of artificial tears: I. Composition and properties. *Adv Exp Med Biol.* 1998a; 438:693-704. 49.
2. Murube J, Murube E, Zhuo C. Classification of artificial tears: II. Additives and commercial formulas. *Adv Exp Med Biol.* 1998b; 438: 705-715.

All relevant disclosure of the above documents are incorporated by reference herein in their entireties and for any purpose including U.S. Pat. Pub. 2012/0070467 which described composition of various ophthalmic compositions and therapeutics which are not related to artificial tear but may be used in the present invention.

Commercial formulation of artificial tears may also be used in the present invention, for example Optive® (Allergen, Inc, Irvine, Calif., USA), or Soothe® (Bausch and Lomb, Rochester, N.Y., USA), or Systane® (Alcon Laboratories, Inc., Fort Worth, Tex., USA).

The drug package is configured to dispense micro-droplets in response to pulse displacement induces on its external surface. The package is made of a thermoplastic polymer such as polyethylene terephthalate, polyethylene or polypropylene. The drug package includes a drug reservoir, an acoustic cavity and an aperture. The drug package further includes a first fluid channel which connects between the drug reservoir and the acoustic cavity and a second fluid channel which connects between the acoustic cavity and the aperture. Drug package contains ophthalmic formulation which fills the volume of the drug reservoir, the acoustic cavity and the channels. The acoustic cavity is comprised of a small fluid enclosure that is sealed by a thin-wall structure. When a pulse displacement is applied onto the thin-wall structure an acoustic pressure is developed within the liquid in the cavity. The acoustic pressure is then propagates through the fluid channel toward the aperture whereat a droplet of liquid is ejected from the aperture. A single droplet is ejected following each pulse displacement. The term pulse displacement means that the displacement has a short duty cycle, preferably between 10-1000 μsec and more preferably between 80-300 μsec (micro-second). The displacement amplitude of the membrane is typically about 1, 2, 3 or 4 µm and generally less than 10 µm Preferably the device operates at high frequency. Droplets ejection frequency is between 1 Hz to 30 KHz.

Droplet volumes are generally between 100 pL to 1000 pL and the size of the aperture is typically between 80 to 120 µm. Strong acoustic pulse may result in formation of small satellite droplets which undesirably disperse in many directions.

In some embodiments the device includes light-emitting-diode (LED) which lit or blinks a few seconds before droplets are ejected. In this way the user is alerted to keep his eyelid wide open for a period of 1, 2 or 3 seconds. In such embodiments the device will dispense automatically every 20, 30, 45, or 60 min. The device will generally dispense in a burst mode which is a predetermined number of oscillations that repeats every predetermined time period. Every burst dispenses a volume that is equal to the arithmetic product of the number of oscillations and the volume of each droplet. Thus for example if a droplet volume is 500 pL and the burst consists of 1000 oscillations then the total volume is 500,000 pL or 0.5 µL (micro-liter). A burst may consist of any number of oscillations but typically less than 10000. This limitation relates to the technical specification of the piezoelectric chip. The time interval between bursts is typically less than 60 min. In some embodiment the device may dispense small volumes sequentially every short time interval without alerting the user. In this way a burst of droplets may miss the surface of the eye due to eyelid blinking without substantially effecting the total dose delivery over a long period.

There is a danger that during a period on non-use the ophthalmic formulation will dry up and clog the aperture, for example during an overnight period. In the present invention the device is configured to eject at least one droplet every 10, 20 or 30 minutes to prevent the ophthalmic formulation from drying up at the aperture.

The actuator comprises of a monolithic co-fired ceramic piezoelectric stack capable of producing large displacement in response to a relatively low voltage input, typically less than 100 volt. The piezoelectric stack (defined by some manufacturers as piezoelectric-chip or piezo chip) is made of an integral stack of multiplicity of piezoelectric elements and therefore its total displacement is the accumulative displacements of all the elements in the stack. In the present invention the piezo stack is preloaded by a spring against the thin wall structure of the acoustic chamber. In this way the drug package can be removed and replaced while the piezo stack can be reused with another drug package. In one embodiment the drug package is manufactured by an aseptic blow-fill-seal process commonly used in packaging of pharmaceutical liquids. Such process is described for example in U.S. Pat. Pubs. 2013/0345672 A1, 2012/0017898, and U.S. Pat. No. 5,624,057, each of which is incorporated herein by reference in its entirety and for any purpose.

The device further includes an electronic circuit that is configured to generate and transmit an electric pulse to the piezoelectric stack. The manufacturing process of the circuit incorporates microelectronics packaging techniques which reduces the size of the circuit. The circuit comprises of a half-bridge driver which includes a half-bridge driver chip and two mosfet transistors. The half-bridge driver receives an input signal and transmits a switching output signals which drives a pair of mosfet transistors sequentially "on" and "off". In this way it translates the low voltage input signal to a high power electrical pulse that is capable of driving the piezo stack. The circuit further includes an inductor that increases the output to higher voltage lever. Preferably the inductance of the inductor and the capacitance of the piezo are tune to operate in resonance at the selected output frequency. The input signal which transmitted to the half bridge driver chip may be generated by a microprocessor or by a signal generator IC (integrated circuit). In one embodiment the driver, the transistors and the microprocessor are fabricated on a single integrated circuit. Preferably such IC is attached and encapsulated directly to a printed circuit board (PCB) utilizing a chip-on-board (COB) packaging process. In the field of microelectronics COB is used to reduce the size of the circuit. In the present invention the input voltage of the circuit is preferably below 5 volt and more preferably below 3 volts and even more preferably below 1.5 volts.

The source of energy is provided by a rechargeable battery such as lithium polymer. Preferably the battery is packaged as flat sheet having a thickness of about 0.5 mm to 2 mm. Preferably the width and length of the battery are equal to the width and length of the PCB. The battery may be recharged wirelessly by induction charging, in that the energy is transmitted by inductive coupling between the device and external charger.

BRIEF DESCRIPTION OF THE DRAWINGS

Having thus summarized the general nature of the invention and some of its features and advantages, certain preferred embodiments and modifications thereof will become apparent to those skilled in the art from the detailed description herein having reference to the figures that follow, of which:

FIG. 6 illustrates a section view marked as Detail-A through the acoustic cavity of the drug package showing a cross sectional shape of the acoustic cavity clamped by the piezo chip in accordance with certain embodiments of the invention.

FIG. 9 illustrates a cross sectional view through the thickness of the drug package showing the fluid channels in accordance with certain embodiments of the invention.

FIG. 9A illustrates a side view of the drug package including the direction of the cross section with respect to respect the illustration in FIG. 9.

FIG. 9B illustrates a top view of drug package in accordance with certain embodiments of the invention.

FIG. 9C illustrates an enlarged view of the fluid channel which includes a detail view of the narrow section that restrict the propagation of acoustic waves.

DETAILED DESCRIPTION OF THE INVENTION

The embodiments described herein relate a device for the delivery of one or more fluid agents to the ocular surfaces for any number of treatments, e.g., dry eye syndrome (DES). Treatments for the condition of chronic DES is described herein for illustrative purposes only as the devices and methods described may be applied to any number of different conditions and for the delivery of any number of agents not limited to the treatment of DES.

In the systems and methods described herein droplets are dispensed in high frequency but in a single drop format. Droplets have ultra small volumes ranging from about a few hundreds pica-liters to about one nano-liters. Droplets of such volume do not cause blinking reflex and delivery in ultra-small volumetric increment can closely simulate the natural tear production.

In the first aspect embodiments the dispensing devices advantageously utilize a disposable, removable or separable drug package while desirably retaining the piezoelectric actuator or transducer for subsequent further uses, thereby providing an economical and cost effective approach with reuse of the piezoelectric actuator or transducer for further operation.

In a second aspect the drug package includes an elongated nozzle or conduit which includes an aperture that is position proximal to the ocular surface while the piezoelectric actuator is positioned distal to the eye.

While the description sets forth various embodiment specific details, it will be appreciated that the description is illustrative only and should not be construed in any way as limiting the invention. Furthermore, various applications of the invention, and modifications thereto, which may occur to those who are skilled in the art, are also encompassed by the general concepts described herein.

Figure 1:
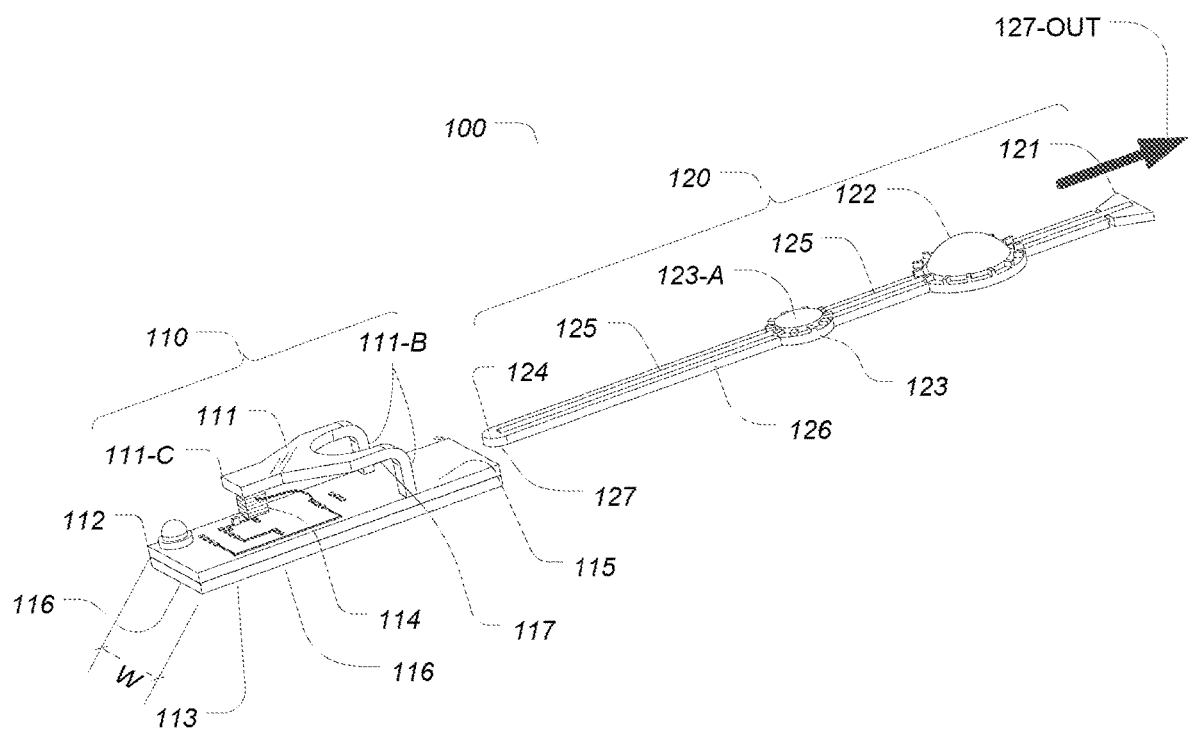
FIG. 1 is a simplified exploded view of piezoelectric actuator and the drug package being separated from each other in accordance with certain embodiments of the invention.
Figure 2:
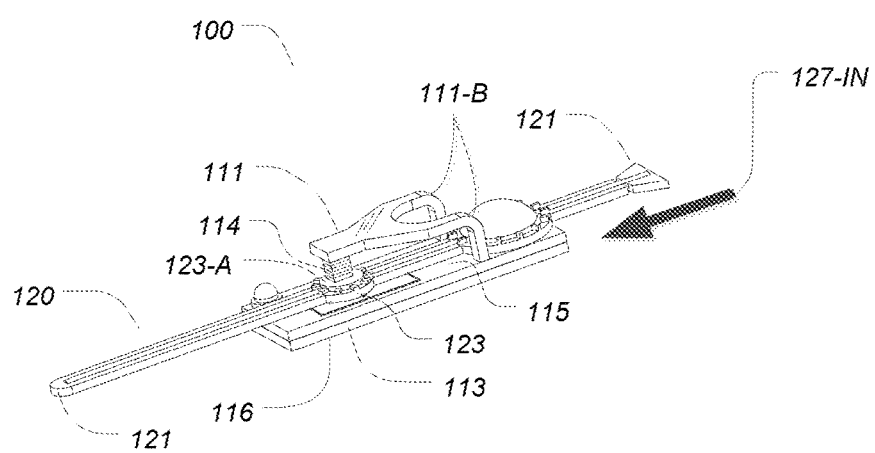
FIG. 2 is a simplified view of the piezoelectric actuator and the drug package operatively coupled in accordance with certain embodiments of the invention.

FIGS. 1 and 2 illustrate a piezoelectric actuator (110) in accordance with some embodiments. The piezoelectric actuator is comprised of a piezoelectric chip (114) that is operatively coupled to a drug package (120) under preloading force. Actuator (110) is configured to generate an acoustic pressure within the drug package to dispense droplets of ophthalmic composition from aperture (124) to the corneal surface of the eye. Piezoelectric actuator (110) can be coupled or decoupled from the drug package as shown in FIGS. 1 and 2 and as discussed further below and herein.

As illustrated in FIG. 1 device (100) includes a drug package (120) and piezoelectric actuator (110). Drug package (120) is comprised of thermoplastic body which includes a blister (122) containing ophthalmic composition to be dispensed. Drug package (110) further includes an elongated nozzle or conduit (126) which extends from the blister and terminates at the tip section (127). Conduit (126) includes an internal fluid channel (not shown) that is in fluid communication with the blister (122). Conduit (126) further includes a dispensing aperture (124) proximal to tip (127) and an acoustic cavity (123) distal to the tip and proximal to the blister (122). In some embodiment the distance between blister (122) and acoustic cavity is about 5-15 mm and the distance between acoustic cavity (123) and aperture is between 30-60 mm. In this way, the piezoelectric actuator (110) is conveniently distal to the dispensing aperture (124) or the eye.

Acoustic cavity (123) comprising a cylindrical chamber sealed by a thin-wall membrane (123-A). Drug package (120) is configured to dispense a micro-droplet each time a pulse displacement is exerted by the actuator (110) onto the surface of the thin-wall membrane (123-A). Such pulse displacement generates an acoustic pressure within the acoustic cavity (123) which then propagates through the fluid in conduit (126) toward the aperture (124) whereat droplets are dispensed in a single drop format at an average rate that is adjusted to supplement for tear production deficiency.

Piezoelectric actuator (110) comprising a piezoelectric clamp and an electronic circuit. The piezoelectric clamp is configured to apply pulse displacements to the acoustic cavity while it is being clamped under spring pressure.

Piezoelectric actuator (110) comprising a printed circuit board (PCB) (115) capable of generating electrical pulses at a selected frequency. Referring to FIG. 2 it can be seen that PCB (115) also functions as rigid substrate for supporting the drug package (120) while being preloaded by the piezoelectric chip (114). It can be seen the piezoelectric chip (114) is attached to the free end of an "L" shape spring member (111) while the opposite end of the spring is split to two legs (111-B) each is attached to the PCB by a solder joints. The piezoelectric chip (114) is attached to the free end (111-C) by a structural epoxy adhesive such as, but not limited to, LOCTITE® Hysol® type E-30CL. Spring member (111) is dimensioned to preload the piezo chip (114) against surface (123-A) by applying about of 5-10 Newton. In some embodiments the spring member (111) is made of beryllium copper. In some embodiments spring member (111) is made of spring steel with nickel plating. The thickness of spring is in the range of 0.3-0.7 mm.

Drug package (120) may be inserted into, or removed from actuator (110) in the directions indicated by arrows (127-IN) and (127-OUT). FIG. 1 illustrates an exploded view of device (100) showing the drug package (120) decoupled from the piezoelectric actuator (110) and FIG. 2 illustrates the drug package (120) operatively coupled to actuator (110).

Piezoelectric chip (114) comprises of a monolithic co-fired piezoceramic stack model PA3CE sold by Thorlabs Inc., Newton, N.J., USA. The chip expands and contracts under the input of an alternating voltage. Co-fired piezoceramic stack produces large displacement, generally in the range of 1-5 micron. In comparison a single crystal piezoceramic element, produces a displacement in the range of a 0.1-0.5 micron, therefore normally requires structural attachment to the oscillating structure. Thus, in the present invention the co-fired piezo-ceramic stack enables the separation of the drug package and an economical, cost effective and practical solution for treatment of DES.

The bottom face of the actuator (110) is attachable to the frame of eyeglasses by means of pressure-sensitive film adhesive (116) provided with protective film (not shown) which is peeled off before the actuator is attached to the earpiece of the eyeglass.

Circuit (115) receives DC power from battery (113) and generates electric pulses which are transmitted to the piezo-electric chip (114) which subsequently generates pulses of displacement against the surface (123-A) of the acoustic cavity (123).

In some embodiments the battery is base on lithium-polymer chemistry and having an electrical capacity of about 70 mAH (milliamp×hours) and about 3 volt output. Lithium polymer batteries may be packaged as a thin flat cell which is consistent with the planer geometry of the PCB. In one embodiment the battery has a thickness range of 0.5 to 2 mm.

The circuit further includes a wireless battery charger configured to recharge battery (113) without making hardware connection. The charger comprising of a wireless receiving coil and a charging circuit (113). Preferably the coil is printed on a circuit board as a spiral conductive layer. A method to optimize the design of such coil and circuit is described in a publication titled: "Design and Optimization of Printed Spiral Coils for Efficient Transcutaneous inductive Power Transmission" IEEE TRANSACTIONS ON BIOMEDICAL CIRCUITS AND SYSTEMS, VOL. 1, NO. 3, SEPTEMBER 2007, which is hereby incorporated by reference herein.

The battery is charged by placing the device in close proximity to a wireless charging pad that meets the Wireless Power Consortium (WPC) standard.

The device is programmed or preset to dispense micro-droplets at an average rate that is adjusted to maintain and restore the normal tear volume on the surface of the dry eye. In some embodiment the device dispense droplet at a frequency of 10 Hz-30 KHz. The device may dispense droplet in a time intervals of 1, 5, 10, 20, 40, 60 min with a typical droplet size is 500 pL (pico-liter). Thus for example, the device may be programmed to dispense an average rate of 1 µL/sec by continuously dispensing droplet of 500 pL at a frequency of 33 Hz. Or at a frequency of 2 KHz and a period of 1 sec every 1 minute. Or pulses at a frequency of 0.1-2 KHz and in an interval that is depended on the tear production deficiency of the patient. Alternatively, the droplets may be administered intermittently, if so desired.

Figure 3:
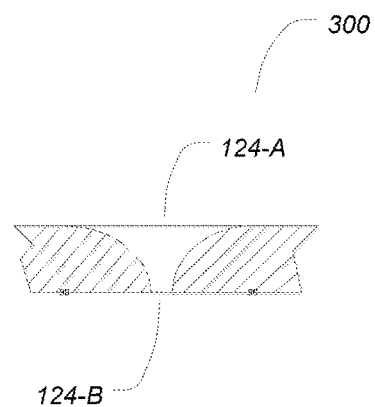
FIG. 3 is a cross sectional view of the dispensing aperture in accordance with certain embodiments of the invention.
Figure 4:
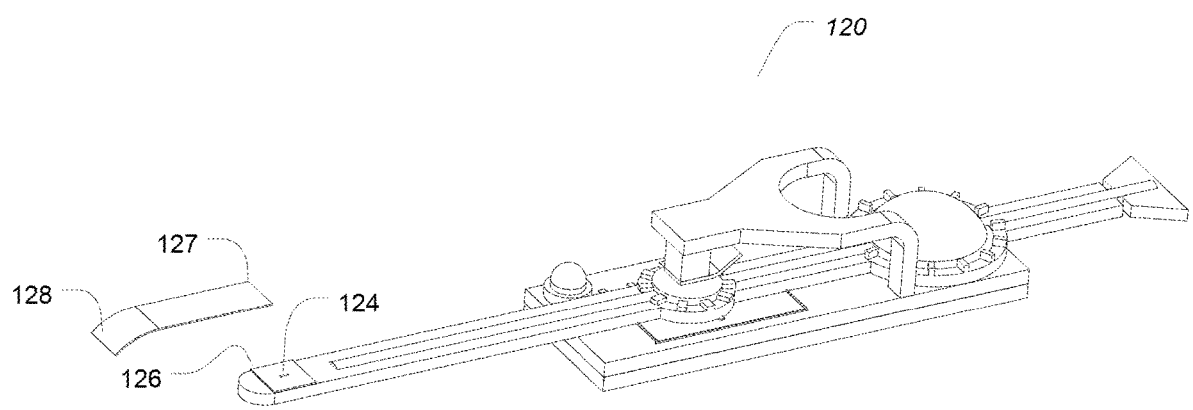
FIG. 4 is a perspective view of the dispensing device showing the protective tape of the aperture in accordance with certain embodiments of the invention.

In one embodiment the device may have one or more apertures. Typically the diameter of each aperture is in the range of 80-120 micron. FIG. 3 illustrates the cross sectional shape of each aperture. It can be seen that the aperture has a generally tapered or flared mouth shape whereas the large opening (124-A) is the fluid inlet and the small opening (124-B) is the droplet outlet. In some embodiments the apertures are formed separately on a polyamide film such as Mylar™ or Kevlar™ (DuPont, Wilmington, Del. USA). The apertures are etched using a laser ablation process commonly used in fabrication of inkjet nozzle plate. FIG. 4 illustrates the polyamide film (126) with the apertures (124). The film is attached by to the drug package by pressure-sensitive adhesive. Drug package (120) further includes a sealing tape (127) that is adhesively attached to a polyamide film (126) over the aperture (124) to hermetically seal the drug package (120) and to prevent bacterial contamination during storage. Sealing tape (127) may be peeled off shortly before drug cartridge is used. Conveniently, the edge (128) of the sealing tape (127) is extended from the edge of drug package, in this way the sealing tape may be easily peeled off by pulling on the extended edge (128) shortly before use. Sealing tape (127) may be labeled to indicate that it should be removed before the drug package is used.

After the sealing tape is removed, there is a danger that the fluid at the aperture may dry up and clog the aperture during a long period of non-use, for example, in an overnight period. To prevent the fluid from drying up the device may be programmed to continuously eject a single drop in a time interval of 10, 20, or 30 minutes. This operation replaces a fluid that is about to dry up with fresh fluid. Since the size of each droplet is small, about 500 pL, the accumulative volume that is dispensed over 12 hour period of non-use is 0.036, 0.018 or 0.0124 (micro-liter). Such volume is negligible compare to the total volume that is stored in the drug package, about 1000 µL (1 ml).

In some embodiments the electronic circuit of the device includes a 2-positions switch. The first is "on" position which sets the device to operate normally during the time the eyeglasses are worn and the second is "sleep" position which sets the device to eject single drops during a period of non-use, as described above.

In some embodiments the circuit includes an optical sensor that detects when the eyeglass are worn. The sensor includes an LED and a light-sensitive sensor. When the eyeglasses are worn the LED illuminates the area of the temple near the corner of the eye. The light is then reflected from the temple and detected by a light-sensitive sensor. When the sensor detects a reflected light it will send a signal to the circuit to switch the device "on", conversely, an absence of reflection will signal the circuit to switch to a "sleep" mode. The LED and the sensor may perform such reflection test periodically every 10, 20, or 30 min. Long intervals are selected to conserve energy. Preferably the LED and the sensor are configured to emit and detect an invisible infra-red light.

Figure 5:
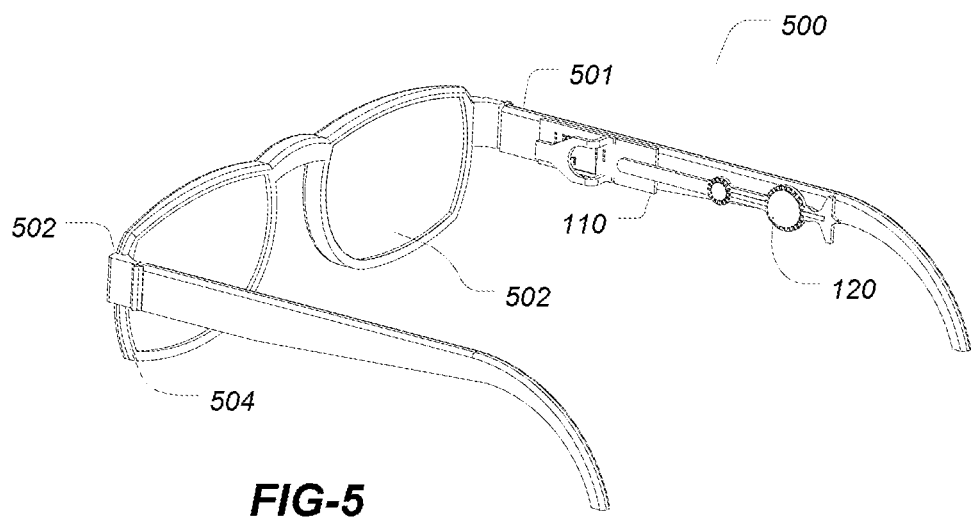
FIG. 5 illustrates the piezoelectric actuator attached to the frame of eyeglasses with the drug package separated in accordance with certain embodiments of the invention.

Referring now to FIG. 5 it can be seen that actuator (110) is attached to the earpiece (501) of the frame of eyeglass (502). In some embodiments actuator (501) is attached by a removable pressure-sensitive double-sided adhesive tape such that one side of the tape is attached to actuator and the opposite side is attached to the earpiece (501). Several water resistant double-sided tapes that may be use include but not limited to model 3M 410M, 3M 4910 VHB or 3M 5952 VHB (3M Maplewood, Minn., U.S.)

Figure 5A:
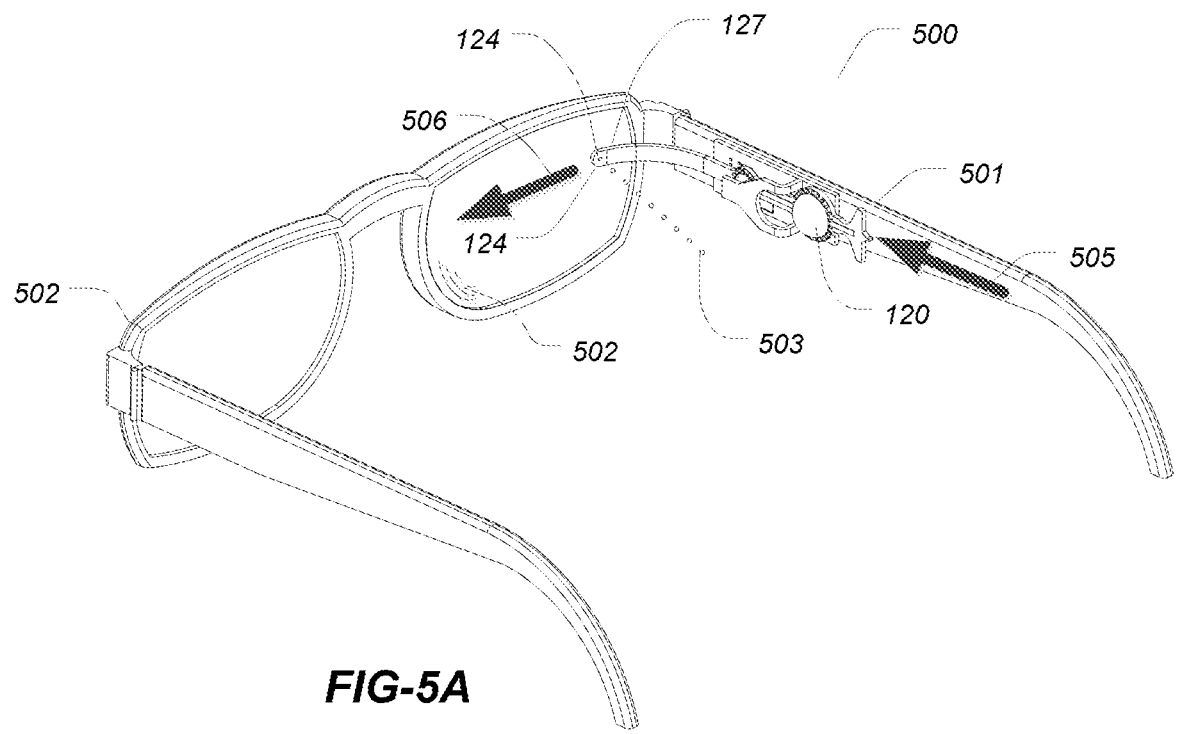
FIG. 5A Illustrates the piezoelectric actuator operatively coupled to the drug package and attached to the frame of eyeglasses in accordance with certain embodiments of the invention.

FIG. 5A illustrates drug package (120) fully inserted into actuator (110). The tip (127) of the drug package (120) first reaches the lens (502) of the eyeglasses and while the drug package is further inserted, tip (127) is bent sideway in the direction indicated by arrow (506) while sliding on the surface of the lens (502). When drug package is fully inserted into the piezoelectric actuator its aperture (124) is oriented toward the eye and droplets (503) are projected onto the surface of the eye. Drug package is inserted until the piezoelectric actuator is stopped and positioned above the acoustic cavity as shown in cross sectional detail view in FIG. 6.

Figure 6A:
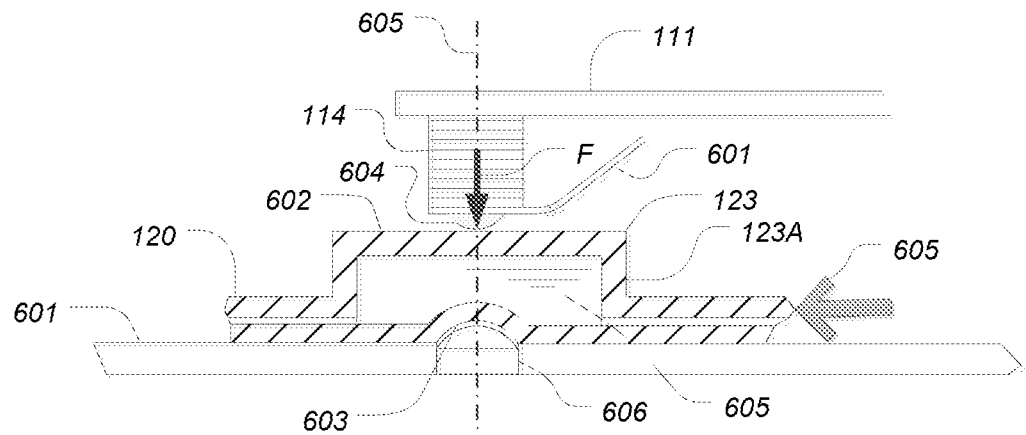
FIG. 6A illustrates the location of Detail-A FIG. 6 in accordance with certain embodiments of the invention.
Figure 6A:
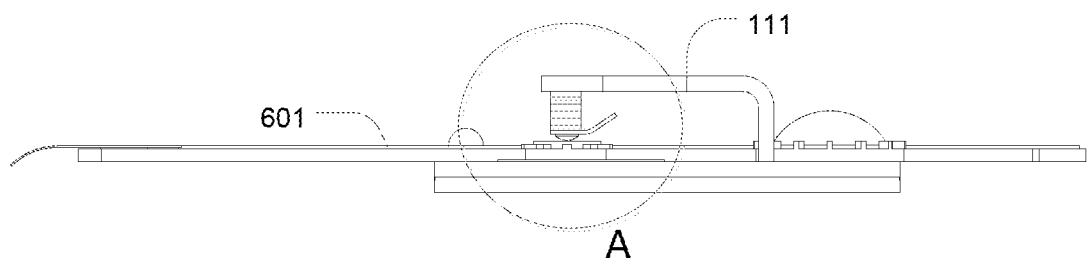

FIG. 6 illustrates a detailed view of the area encircled in FIG. 6A showing drug package (120) operatively coupled by the piezoelectric chip (114. It can be seen that acoustic chamber (123) is clamped between piezo chip (114) and the surface of the printed circuit board (PCB) (601). A spring member (111) provides a clamping force (F) of about of 10 Newton. Acoustic chamber (123) comprises a cylindrical enclosure (123A) and two surfaces, the first is a planer surface (602) which seals one face of the chamber and the second is a concave surface (603) which seals the opposite side of the chamber. A dome shape-member (604) is attached to piezo chip (114) The spherical shape of the dome transmits the displacement of the piezo chip in a direction normal to the surface of the acoustic chamber (601) as indicated by vector (F). PCB (601) is provided with a dowel pin (606) which has a spherical endpoint configured to engage with the concave surface of the acoustic chamber to lock the drug package in place by restricting its lateral movements. Dowel pin (606) however allows a rotational displacement of the drug package about its axis (605). Such rotational displacement may be used for fine adjustment of the drug package with respect to the eye as explained in more details hereafter.

Drug package (120) is inserted into the actuator in the direction indicated by arrow (605). Drug package slides over the surface of the PCB (601) until dowel pin (606) snaps into the concave surface (603). Dome member (604) includes a leading edge (601) which guides the package to slide under piezo chip (114).

Figure 7:
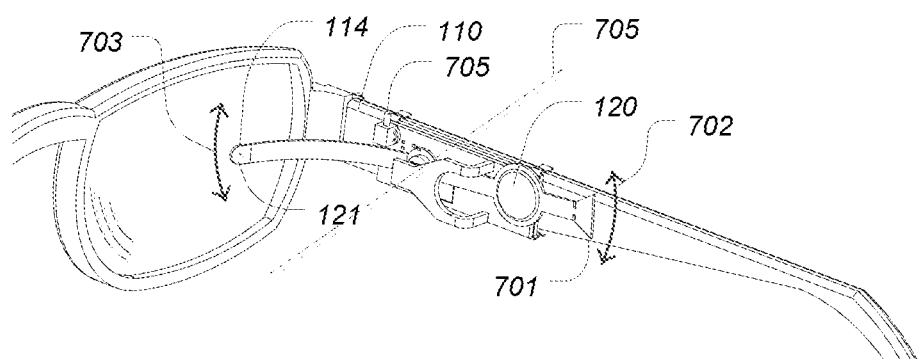
FIG. 7 illustrates an adjustment method of the drug package with respect to the eye while piezoelectric actuator and the drug package are operatively coupled.

FIG. 7 illustrates drug package (120) operatively coupled to piezoelectric actuator (110). As described in relation to FIG. 6 drug package can rotate about the axis of the dowel pin (705). Such rotational displacement may be used to make fine adjustment of the aperture (114) with respect to the eye. Edge (701) of the drug package can be pushed clockwise or counterclockwise as indicated by the arrows (702), subsequently, tip (121) of drug package (120) which includes the dispensing aperture (114) will rotates in the opposite directions as indicated by the arrow (703). Actuator (110) is further provided with a momentary switch (705) which is configured to drive the piezo actuator to dispense a burst of droplets. In this way the user may check if the nozzle is properly adjusted and droplets are reaching the eye or if further adjustments (702) are needed. The switch is configured to dispense about 5000 droplets within about 2 second producing a volume of 2 µL which can be detected or sensed by the user.

Figure 8:
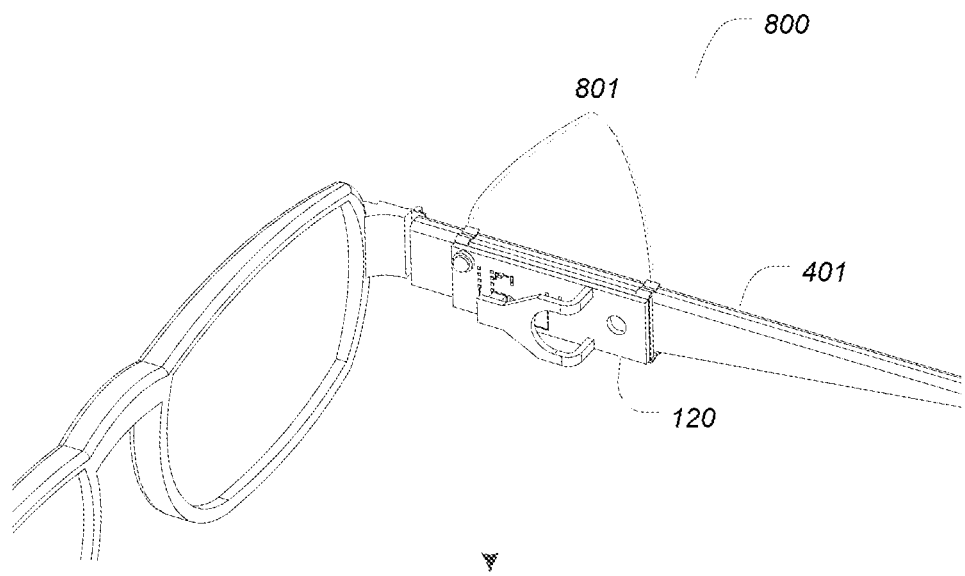
FIG. 8 illustrates an alternative attachment of the piezoelectric actuator to the frame of eyeglasses using spring clips in accordance with certain embodiments of the invention.

FIG. 8 illustrates an alternative method of attaching the actuator (120) onto the earpiece (401) of eyeglass. In some embodiments actuator (120) includes two "U" shape spring-clips (801) which clip or snap around and over the edges of the earpiece (401).

FIGS. 9 and 9A illustrate a cross sectional view through the thickness of drug package (120) in the direction indicated in by arrows A-A. FIG. 9 illustrated a cross sectional view showing the fluid channel (901) that extends along drug package (122) from drug reservoir (122) through acoustic cavity (123) and to aperture (124) The section of channel (901) that extends between the drug reservoir (122) and the acoustic cavity (123) is shown in an enlarged detailed view in FIG. 9C marked Detail-B. Referring to FIG. 9C it can be seen that the section of the channel that connects between the drug reservoir (122) and the acoustic cavity (123) has a restriction (901-N). Restriction (901-N) restricts the propagation of acoustic pressure wave from acoustic cavity (123) to reservoir (122). This limits the acoustic pressure dissipation into the drug reservoir and the pressure wave that reaches the aperture (124) is desirably more intense In some embodiment the cross section area of channel (901) is between 0.25-1 mm while cross section of the restricted section (901-N) is about 50-90% smaller. The cross sectional area of the restriction (901-N) is the effective area through which the acoustic wave propagates as indicated by the arrow symbol R-R and C-C. The cross sectional shape may be but not limited to circulator or rectangular shape.

The end section of channel (901) is used as a venting port to the drug reservoir (122). The end section of the channel (901-V) extends from the drug reservoir to tab section (903).

Before use the tab is broken and the opening of channel (901-V) is exposed to the atmosphere. Venting is necessary to prevent vacuum build up in the drug reservoir during use.

In some embodiment the diameter of the drug reservoir (122) is between 8 mm to 14 mm and its volume is in the range between 0.5 mL to 1.5 mL. In some embodiment the diameter the acoustic cavity is between 5-8 mm and its volume is 30-100 µL.

The length of the channel (901) between the acoustic cavity (123) and the aperture (114) is designated by the letter L in FIG. 9. In some embodiments the operating frequency is the natural frequency of the fluid in the channel (901). The natural frequency is govern by the following equation:

$$f := \frac{i \cdot C}{2 \cdot L} \tag{1}$$

C=1500 m/sec (speed of sound in aqueous composition)
L=40 mm (length L of the channel (901))
i=1, 2, 3, . . . , n When substituting C, L and i=1 it can be found that the natural frequency of the fluid in the channel (901) is 19,500 Hz, therefore the operating frequency of the electronic circuit should also be 19,500 Hz. The volume of liquid dispense is determined by the number of cycles that the piezoelectric actuator operates in this frequency.

All the internal fluid passage shown in cross sectional view of FIG. 9 including fluid channels (901), drug reservoir (122) and acoustic cavity (123) are treated with hydrophilic coating which increase the surface tension produces a strong capillary force through all the internal fluid passages of the drug package (120) as well as strong fluid-solid coupling in the acoustic cavity. Particularly effective coating is Hydrophil™ made by Lotus Leaf Coating Inc. New Mexico, USA.

Figure 10:
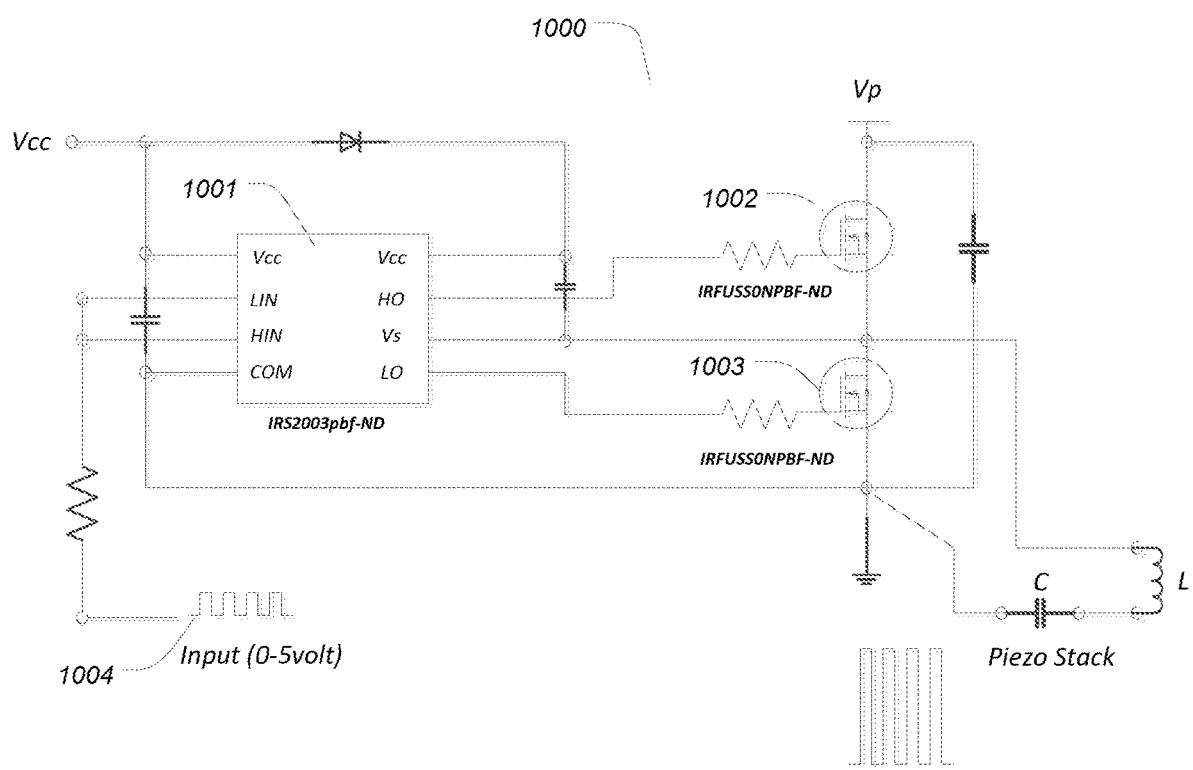
FIG. 10 illustrates a schematic diagram of the electronic circuit of the piezoelectric actuator in accordance with certain embodiments of the invention.

FIG. 10 illustrates a schematic diagram of the electronic circuit. The circuit is configured to generate and transmit an electric pulse to the piezoelectric chip. The manufacturing process of the circuit incorporates microelectronics packaging techniques which reduces the size of the circuit. Circuit (1000) comprises a half-bridge driver which includes a half-bridge driver chip (1001) and two mosfet transistors (1002) and (1003). The transistors are connected directly to the battery voltage source (Vp). The half-bridge driver receives a square wave signal (1004) and transmits a switching signal which drives a pair the transistors sequentially "on" and "off". In this way the battery source voltage (Vp) and current capacity is switched at high frequency providing a powerful electrical pulse. The circuit further includes an inductor (L) that is connected in series to the piezo chip (C) and together defines an L-C resonance circuit. The inductance (L) and the capacitance of the piezo chip (C) resonate at an operating frequency. In some embodiment the operating frequency is 19500 Hz which is the resonance frequent of the fluid in the drug package as described in relation to FIG. 9. The capacitance of the piezo chip model PA3CE is 30 nF (Thorlabs Inc., Newton, N.J., USA) using the resonance frequency calculation for LC circuit in series:

$$f := \frac{1}{2 \cdot \pi \sqrt{LC}} \tag{2}$$

Solving for the inductance L:

$$L := \frac{\left(\frac{1}{2\pi f}\right)}{C} \quad (3)$$

$$L = 2.22 \text{ mH}$$

An inductor that has a value of 2.22 mH connected in series to the piezo chip will cause the circuit to resonate and as a result the voltage level of the battery will increase typically by 5, 10, 20 times. In the present invention the size of the droplets is in the range of 500 pL (pico-Liter). In comparison, the lachrymal tear flow is about 1 μL/min, thus such volume can be created by generating 2000 pulses at a frequency of 19500 Hz during a period of about 0.1 sec.

The input signal (1004) may be generated by a microprocessor or by a signal generator IC (integrated circuit). In one embodiment the driver, the transistors and the microprocessor are fabricated on a single integrated circuit. Preferably such integrated circuit (IC) that is attached and encapsulated directly to a printed circuit board (PCB) utilizing a chip-on-board (COB) packaging process. In the field of microelectronics COB is used to reduce the size of the circuit. In the present invention the input voltage of the circuit is preferably below 5 volt and more preferably below 3 volts and even more preferably below 1.5 volts.

The source of energy is provided by a rechargeable battery such as lithium polymer. Preferably the battery is packaged as flat sheet having a thickness of about 0.5 mm to 2 mm. Preferably the width and length of the battery are sustainably equal to the width and length of the PCB. The circuit further has a power receiving coil coupled to the battery and charges the battery upon receiving wireless power. An wireless charging system described in U.S. Pat. Pub. 2014/0224267 A1, which is incorporated by reference herein in its entirety and for any purpose.

Adjustment of the droplet volume per and the dispensing frequency can be accomplished by programming the device according to the tear production deficiency of each DES patient. Such programming may be done by expert; however in some cases there may be a need to make further adjustments, depending for example on the environmental condition such as ambient temperature, humidity, wind or ventilation air flow which effect tear evaporation rate.

In some embodiments the electronic circuit is provided a with a remote control function that communicates with a mobile device which enables convenient control the droplets dispensing functions through various icons on a screen display. A mobile communication device may be a Smartphone, certain personal computers, or tablets equipped with near-field-communication (NFC) hardware and software which are based on near-field magnetic induction (NFMI) method or other radio communication methods such as Bluetooth, Wi-Fi or ZigBee.

Figure 11:
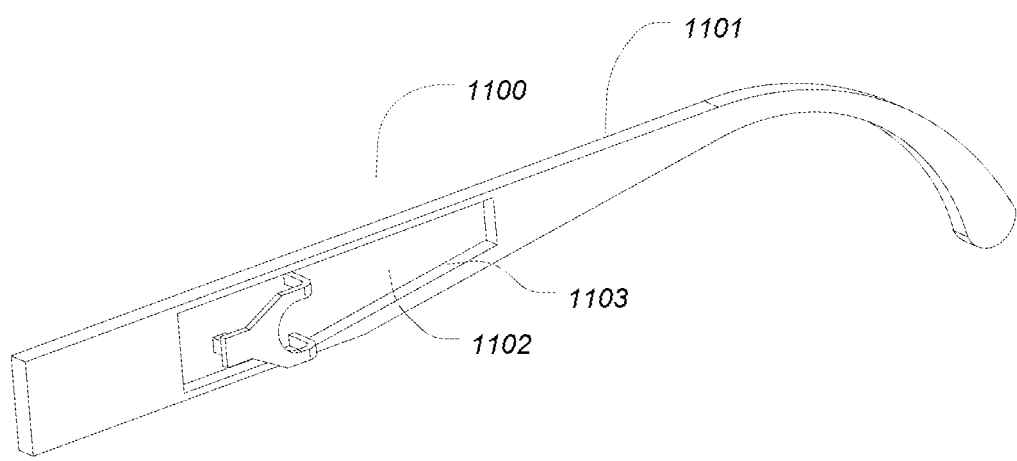
FIG. 11 illustrates the piezoelectric actuator integrally installed in a cavity within the earpiece of eyeglasses in accordance with certain embodiments of the invention.

FIG. 11 illustrates an earpiece of eyeglasses integrally incorporates the piezoelectric actuator. Earpiece (1101) includes a pocket or a recess (1103) that provides an enclosure or a housing for the battery and for the electronic circuit (1102). This embodiment eliminates the need to connect the piezoelectric actuator by means of an adhesive film or a clip as described earlier.

The applications of the disclosed invention discussed above are not limited to the embodiments described, but may include any number of other applications and uses. Modification of the above-described methods and devices for carrying out the invention, and variations of aspects of the invention that are obvious to those of skill in the arts are intended to be within the scope of this disclosure. Moreover, various combinations of aspects between examples are also contemplated and are considered to be within the scope of this disclosure as well.

What is claimed is:

1. A system for emitting a fluid, comprising:
   (a) an actuator having a contact portion; and
   (b) a drug package comprising:
      (i) a fluid reservoir near or at one end of the drug package;
      (ii) an elongated conduit extending from the fluid reservoir and terminating in a tip section having a single aperture, wherein the elongated conduit comprises an internal fluid channel in fluid communication with the interior of the fluid reservoir and the aperture;
      (iii) an acoustic cavity comprising a cylindrical chamber having an upper circular face sealed by a thin-wall membrane, wherein the acoustic cavity is positioned along the internal fluid channel between the fluid reservoir and the tip section; and
      (iv) a fluid ophthalmic drug composition present in the fluid reservoir, acoustic cavity and internal fluid channel,
   wherein the drug package is removably separable from the actuator and is also positionable to align thin-wall membrane of the acoustic cavity with the contact portion of the actuator such that displacement induced on the external surface of the thin-wall membrane by the contact portion of the actuator transmits one or more acoustic pulses through the fluid ophthalmic drug composition in the internal fluid channel to eject fluid through the aperture to produce a stream.

2. The system of claim 1 wherein the actuator comprises a piezoelectric chip.

3. The system of claim 2 wherein the piezoelectric chip is configured to have a displacement of 1-5 microns.

4. The system of claim 1 wherein the acoustic cavity further comprises a concave surface opposite the upper surface.

5. The system of claim 4 wherein a distance between the fluid reservoir and the acoustic cavity is about 5-15 mm.

6. The system of claim 4 wherein a distance between the acoustic cavity and aperture is about 30-60 mm.

7. The system of claim 4 further comprising a restriction positioned along the conduit between the acoustic cavity and the fluid reservoir to restrict a propagation of acoustic pressure waves into the fluid reservoir.

8. The system of claim 4 wherein the acoustic cavity has a volume of 30-100 μL.

9. The system of claim 1 wherein the fluid reservoir has a volume of about 1000 μL.

10. The system of claim 1 wherein the aperture has a diameter of 80-120 micron.

11. The system of claim 1 wherein the actuator is programmed to dispense the fluid through the aperture at a frequency of 10 Hz-30 KHz.

12. The system of claim 1 wherein the fluid is ejected as a stream of micro-droplets.

13. The system of claim 12 wherein the actuator is programmed to eject the fluid in a single drop format to produce a stream of micro-droplets.

14. The system of claim 12 wherein the micro-droplets range in volume from 100 pL to 1000 pL.

15. The system of claim 1 wherein the actuator is programmed to eject the fluid as a stream of micro-droplets at pre-determined time intervals.

16. The system of claim 1 further comprising an eyeglass frame upon which the system is attached.

17. The system according to claim 16 wherein the system is attached to an earpiece of the eyeglass frame.

18. The system according to claim 17 wherein the system is attached to the earpiece in a manner such that the drug package reaches a lens of the eyeglass frame and the tip section is bent sideways such that the aperture is oriented toward the eye.

19. A method of emitting a fluid, comprising:
   aligning an actuator having a contact portion with a drug package comprising an aperture at a first end comprising a tip section of the drug package and a fluid reservoir near or at a second end of the drug package, wherein the fluid reservoir contains a volume of a fluid ophthalmic drug composition and the drug package is removably separable from the actuator; and
   displacing the contact portion of the actuator on the external surface of the drug package to cause one or more acoustic pulses to be transmitted through the fluid ophthalmic drug composition in the drug package such that fluid is ejected through the aperture as a stream;
   wherein the actuator is attached to an earpiece of an eyeglass frame and the drug package reaches a lens of the eyeglass frame and the tip section is bent sideways such that the aperture is oriented toward the eye.

20. The method of claim 19 further comprising removing the drug package from the actuator.

21. The method of claim 19 wherein displacing comprises actuating a piezoelectric chip which displaces the contact portion.

22. The method of claim 21 wherein displacing comprises displacing the contact portion 1-5 microns.

\* \* \* \* \*